United States Patent [19]
Sisti et al.

[11] Patent Number: 6,133,462
[45] Date of Patent: Oct. 17, 2000

[54] C-7 CBZ BACCATIN III AND PRODUCTION METHOD THEREFOR

[75] Inventors: Nicholas J. Sisti, Boulder, Colo.; Charles S. Swindell, Merion, Pa.

[73] Assignees: NaPro BioTherapeutics, Inc., Boulder, Colo.; Bryn Mawr College, Bryn Mawr, Pa.

[21] Appl. No.: 08/922,684

[22] Filed: Sep. 2, 1997

Related U.S. Application Data

[63] Continuation-in-part of application No. 08/719,488, Sep. 25, 1996, Pat. No. 5,750,737.

[51] Int. Cl.[7] .................................................. C07D 305/14
[52] U.S. Cl. ............................................ 549/510; 549/511
[58] Field of Search ...................................... 549/510, 511

[56] References Cited

U.S. PATENT DOCUMENTS

| | | | |
|---|---|---|---|
| Re. 34,277 | 6/1993 | Denis et al. | 549/510 |
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 4,924,012 | 5/1990 | Denis et al. | 549/510 |
| 4,960,790 | 10/1990 | Stella et al. | 514/449 |
| 5,015,744 | 5/1991 | Holton | 549/510 |
| 5,136,060 | 8/1992 | Holton | 549/510 |
| 5,229,526 | 7/1993 | Holton | 549/213 |
| 5,399,726 | 3/1995 | Holton et al. | 549/510 |

FOREIGN PATENT DOCUMENTS

| | | |
|---|---|---|
| 0 400 971 | 12/1990 | European Pat. Off. . |
| 0 528 729 A1 | 2/1993 | European Pat. Off. . |
| WO 91/13066 | 9/1991 | France . |
| 2687150 | 8/1993 | France . |
| WO93/16060 | 8/1993 | WIPO . |
| WO 94/18186 | 8/1994 | WIPO . |

OTHER PUBLICATIONS

"A Chemoselective Approach to Functionalize the C–10 Position of 10–Deacetylbaccatin III, Synthesis and Biological Properties of Novel C–10 Taxol Analougues", Kant et al, Tetrahedron Letters, vol. 35, No. 31, pp. 5542–5546, 1994.

"Taxol Photoaffinity Label: 7–(P–Azidobenzoyl)Taxol Synthesis and Biological Evaluation", Georg et al, Bioognic & Medicinal Chemistry Letters, vol. 2. No. 7, pp. 735–738, 1992.

"Highly Sterocontrolled and Efficient Preparation of the Protected, Esterification Ready Docetaxel (Taxotere) Side Chain", Kanazawa et al., J. Org. Chem, vol. 59, No. 6, pp. 1238–1240, 1994.

"Biologically Active Taxol Analogues with Deleted Apring Side Chain Substituents and Variable C=—2' Configuratoins", Swindell et al, Journal of Medicinal Chemistry, 1991, VO. 34, No. 3, pp. 1176–1184.

"New and Efifcient Approaches to the Semisynthesis of Taxol and its C–13 Side Chain Analogs by Means of B Lactam Synthon Method", Ojima et al, Tetrahedron, vol. 48, No. 34, pp. 6985–7012, 1992.

"Improved Protection and Esterifcation of a Precursor of the Taxotere and Taxol Side Chains", Commercon et al., Tetrahedron Letters, vol. 33, No. 36, pp. 5185–5188, 1992.

"Novel Biologically Active Taxol Analogues:Baccatin III 13–(N–(P–Chlorobenzoyl)–(2'R, 3'S)–3'–Phenylisoserinate) and Baccatin III 13–(N–Benzoyl)–(2'R,3'S) –3'–(P–Chlorophenyl)Isoserinate)", Georg et al, Bioorganic & Medicinal Chemistry Letters, vol. 2, No. 4, pp. 295–298, 1992.

"Application of the Vicinal Oxyamination Reaction with Asymmetric Induction to the Hemisynthesis of Taxol and Analogues", L. Mangatal et al, Tetrahedron, vol. 45, No. 13, pp. 4177 to 4190, 1989.

"Protection for the Hydroxyl Group, Including 1,2– and 1,3–Diols", Greene, Protective Groups in Organic Synthesis, Second Edition, 1991.

Modified Taxols. 3. Preparation and Acylation of Baccatin III:, Magri et al, J. Org. Chem., 1986, 51, 3239–3242.

"The Chemistry of Taxol", Kingston, Pharma:Ther., vol. 52, pp. 1–34 1992.

"Taxol Chemistry. 7–O–Triflates as Precursors to Olefins and Cyclopropanes", Johnson et al, Tetrahedron Letters, vol. 35, No. 43, pp. 7893–7896, 1994.

"Selectively reductive cleavage of the protected taxol side chain with sodium borohydride", Cheng–Zhi Yu et al., Chinese Journal of Chemistry, vol. 14, No. 4, 1996, pp. 381–384.

"Selectively reductive cleavage of the protected taxol side chain with sodium borohydride", Cheng–Zhi Yu et al., Chemical Abstracts, vol. 125, No. 21, 1996, Abstract No. 276218J.

Primary Examiner—Ba K. Trinh
Attorney, Agent, or Firm—Timothy J. Martin; Michael R. Henson; Mark H. Weygandt

[57] ABSTRACT

A compound for use in the production of taxanes and intermediates therefor having the formula:

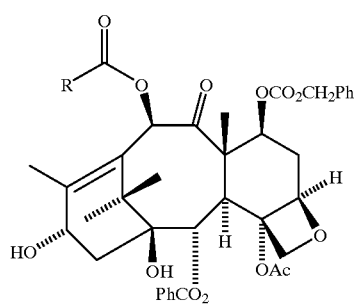

wherein R is an alkyl group.

14 Claims, No Drawings

C-7 CBZ BACCATIN III AND PRODUCTION METHOD THEREFOR

RELATED APPLICATION

This application is a continuation-in-part of application Ser. No. 08/719,488 filed Sep. 25, 1996 now U.S. Pat. No. 5,750,737 and entitled Method for Paclitaxel Synthesis.

FIELD OF THE INVENTION

The present invention is directed to intermediate compounds useful in the production of the anti-neoplastic compound paclitaxel. More particularly, it is directed C-7 CBZ baccatin III, and analogs thereof, as well as methods of producing the same.

BACKGROUND OF THE INVENTION

Various taxene compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity. Paclitaxel has the formula:

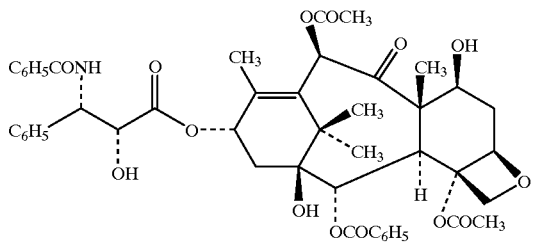

Paclitaxel is a naturally occurring taxane diterpenoid which is found in several species of the yew (genus Taxus, family Taxaceae). Unfortunately, the concentration of this compound is very low. The species of evergreen are also slow growing. Even though the bark of the yew trees typically exhibit the highest concentration of paclitaxel, the production of one kilogram of paclitaxel requires approximately 16,000 pounds of bark. Thus, the long term prospects for the availability of paclitaxel through isolation are discouraging.

While the presence of paclitaxel in the yew tree is in extremely low concentrations there are a variety of other taxane compounds, such as Baccatin III, cephalomanine, 10-deacetylbaccatin III, etc., which are also able to be extracted from the yew bark. Some of these other taxane compounds are more readily extracted in higher yields. Indeed, a relatively high concentration of 10-deacetylbaccatin III can be extracted from the leaves of the yew as a renewable resource.

In order to successfully synthesize paclitaxel, convenient access to a chiral, non-racemic side chain and an abundant natural source of a usable baccatin III backbone as well as an effective means of joining the two are necessary. However, the esterification of the side chain to the protected baccatin III backbone is difficult because of the sterically hindered C-13 hydroxyl in the baccatin III backbone which is located within the concave region of the hemispherical protected baccatin III skeleton.

One technique for the semi-synthesis of paclitaxel is found in co-pending patent application Ser. No. 08/483,081. In this application paclitaxel is synthesized by joining C-7 TES baccatin III with N-carbamate protected C-2' hydroxyl benzyl-type protected (2R,3S)-3-phenylisoserine, where the C-2' hydroxyl is protected by a hydrogenable benzyl-type group such as benzyloxymethyl (BOM) or benzyl. Following the esterification of the protected baccatin III and the protected side chain, the compound may be suitably deprotected, acylated, and further deprotected to yield paclitaxel.

While the existing techniques for synthesizing paclitaxel certainly have merit, there is still a need for improved chemical processes which can produce this anti-cancer compound and intermediates useful in the synthesis and semi-synthesis thereof. The present invention is directed to the synthesis of C-7 CBZ protected baccatin III, which can then be esterified with a suitably protected side chain, then the resulting compound deprotected to yield paclitaxel or other analogs.

SUMMARY OF THE INTENTION

It is an object of the present invention to provide a new compound useful in synthesizing paclitaxel.

It is another object of the present invention to provide methods for producing intermediate that can then be used to synthesize paclitaxel and paclitaxel analogs.

Another object or the present invention is the production of new and useful compounds C-7 CBZ baccatin III and analogs thereof.

It is yet another object of the present invention to provide methods for producing C-7 CBZ baccatin III and analogs which are simplified and which may be suitable intermediates for large scale production of paclitaxel and analogs for anti-neoplastic applications.

The present invention thus is directed to a new chemical compound having the formula:

Formula 1

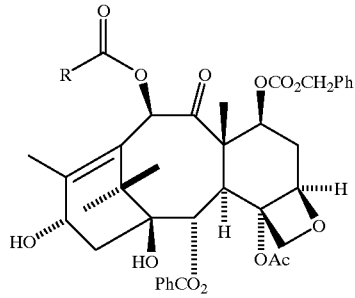

wherein R is an alkyl group. Preferably, the alkyl group is a methyl group.

The invention is also directed to a method of producing the compound of Formula 1, especially where R is a methyl group. This is accomplished by selecting a starting compound from a group consisting of baccatin III and 10-deacetylbaccatin III. The starting compound is then dissolved in a first solvent to form a first solution. The first solution is cooled to a temperature of −20° C. or less, and thereafter an alkyl lithium base is added to the first solution thereby to form an intermediate compound having a lithium alkoxide at the C-7 position thereof. The broad method includes the step of selectively acylating, at the C-10 position, any of said first intermediate compound present in the first solution where the intermediate compound does not already have an acetyl group at the C-10 position thereby to produce a second solution of C-7 lithium alkoxide of baccatin III. Finally, the broad method includes the step of adding CBZ-Cl to the second solution to form a third solution of C-7 CBZ baccatin III.

In the general method, it is preferred that the first solvent is tetrahydrofuran. It is preferred to cool the first solution to a temperature of at least −40° C. Where the starting compound is 10-deacetylbaccatin III, it is preferred to add at least two equivalents of the n-butyl lithium.

The general method described above can be expanded by including the step of warming the third solution to at least 0° C. over a selected interval of time, such as one hour. Further, the third solution may then be quenched with an agent effective to eliminate any excess of the alkyl lithium base and any excess of the CBZ-Cl thereby to form a fourth solution. The method then includes the step of concentrating the C-7 CBZ baccatin III from the fourth solution to a first residue, and the step of purifying the C-7 CBZ baccatin III from the first residue. This purification may be accomplished by column chromatography or recrystallization.

These and other objects of the present invention will become more readily appreciated and understood from a consideration of the following detailed description of the exemplary embodiment

DETAILED DESCRIPTION OF THE INVENTION

The present disclosure is broadly directed to new chemical compounds, namely, C-7 CBZ baccatin III and analogs thereof. The invention concerns a method of producing these chemical compounds. Such compounds are demonstrably useful for the efficient production of paclitaxel and paclitaxel analog. More specifically, the present invention discloses C-7 CBZ baccatin III as a useful intermediate in the production of paclitaxel. The C-7 CBZ baccatin III maybe esterified with an N-CBZ-3-phenylisoserine acid having a hydrogenable benzyl-type hydroxyl protecting group at C-2' to join the side chain at the C-13 hydroxyl of the protected baccatin III backbone. The general processes described herein involves the production of the C-7 CBZ baccatin III backbone, its condensation with a suitably protected N-CBZ-3-phenylisoserine acid having the hydrogenable benzyl-type protecting group C-2' and the subsequent deprotection to yield paclitaxel.

A. Production of C-7 CBZ Protected Baccatin III

According to the present invention, two alternative routes are described for producing C-7 CBZ protected baccatin III. On one hand, baccatin III can be protected at the C-7 site to yield C-7 CBZ baccatin III. On the other hand, 10-deacetylbaccatin III (10-DAB) can be directly converted to C-7 CBZ baccatin III without going through a baccatin III intermediate. Production from baccatin III is advantageous for its yield and simplicity.

The method using 10-deacetylbaccatin III has an advantage since 10-deacetylbaccatin III is much more naturally abundant, and thus less expensive, than baccatin III; however, this alternative method has a reduced yield.

Route 1

Using Baccatin III

C-7 CBZ baccatin III has the formula:

[Chemical structure of C-7 CBZ baccatin III with AcO, O, OCO$_2$CH$_2$Ph, HO, HO, PhCO$_2$, OAc, H groups]

and can be synthesized from baccatin III according to the following reaction:

Reaction I

[Chemical structures showing baccatin III starting material with AcO, O, OH, HO, HO, PhCO$_2$, OAc, H groups, arrow to product C-7 CBZ baccatin III with AcO, O, OCO$_2$CH$_2$Ph, HO, HO, PhCO$_2$, OAc, H groups]

Baccatin III is dissolved in anhydrous THF (tetrahydrofuran) to form a first solution, which is cooled under a nitrogen atmosphere to a reduced temperature of less than −20° C. n-Butyl lithium. (1.6 M in hexane) is then added dropwise to the first solution to form a second solution, which is stirred for approximately 5 minutes at the reduced temperature, Benzyl chloroformate (CEZ-Cl) is added dropwise to the second solution to form a third solution which is then stirred and allowed to warm to 0° C. over approximately one (1) hour. The third solution is quenched with cold saturated ammonium chloride to eliminate any excess n-butyl lithium and CBZ-Cl, and the mixture is concentrated under vacuum to yield a first residue. This first residue is next taken up in ethyl acetate and washed once with water to remove unwanted salts. Next, the residue is washed with brine. The organic layer is then dried and concentrated under vacuum to yield a second residue. The second residue is recrystallized or column chromatographed with ethyl acetate:hexane to give C-7 CBZ baccatin III as a white solid.

Route 2

Using 10-deacetylbaccatin III

Alternatively, C-7 CBZ baccatin III can be synthesized directly from 10-deacetylbaccatin III as follows:

Reaction II

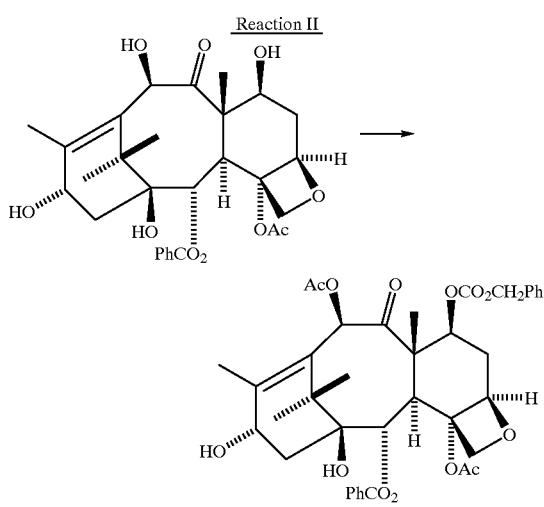

Here, 10-DAB is dissolved in THF to form a first solution which is cooled to a reduced temperature of less than −20° C. under a nitrogen atmosphere. At least 2 equivalents of n-butyl lithium (1.6 M in hexane) are then added dropwise to the first solution to form a second solution which is then stirred for approximately 5 minutes at the reduced temperature. Preferably, acetyl chloride (1 equivalent) is added to the second solution to form a third solution which is stirred at the reduced temperature for approximately 30 minutes. Alternatively, acetic anhydride (1 equivalent) may possibly be used in place of the acetyl chloride to acylate the 10-DAB. In either case, benzyl chloroformate (1 equivalent) is next added, and this fourth solution is stirred for an additional thirty (30) minutes at the reduced temperature and then warmed to 0° C. over thirty (30) minutes. The fourth solution is then quenched with cold saturated ammonium chloride at the reduced temperature to remove any excess n-butyl lithium, acetyl chloride and CBZ-Cl; this mixture is then warmed to room temperature. The solvent is removed under vacuum to yield an initial residue which is taken up in ethyl acetate and washed with water to remove unwanted salts. The residue is then washed with brine, dried and concentrated under vacuum to yield a final residue. The final residue is chromatographed (silica gel hexanes:ethyl acetate) to yield C-7 CBZ baccatin III. It is important to note that this method represents a direct synthesis of C-7 CBZ baccatin III from 10-DAB, as the intermediate formed in this reaction is a C-7 lithium alkoxide of baccatin III, that is, the intermediate is not baccatin III itself.

While both Routes 1 and 2 specifically are directed to the production of baccatin III, it should be apparent to the ordinarily skilled person that baccatin III analogs can be produced from the Route 2 process simply by substituting the appropriate acid chloride to the second solution fin Route 2. This would result in the formation of analogues with different alkyl groups at C-10.

It should now be appreciated that both Route 1 and Route 2 to the production of C-7 CBZ baccatin III can be expressed as a generalized method. This method starts with a step of dissolving a starting compound selected from a group consisting of baccatin III and 10-deacetylbaccatin III in a first solvent to form a first solution. The first solution is then cooled to a temperature of −20° C. or less. Thereafter, an alkyl lithium base is added to the first solution thereby to form an intermediate compound having a lithium alkoxide at the C-7 position thereof. Next, as would be required for the 10-DAB starting compound, the method includes selectively acylating, at the C-10 position, any of the first intermediate compound present in the first solution where the intermediate compound does not already have an acetyl group at the C-10 position thereby to produce a second solution of C-7 lithium alkoxide of baccatin III. Of course, where the starting compound is baccatin III, the C-10 position already has an acetyl group. In any event, the method includes a step of thereafter adding CBZ-Cl to the second solution to form a third solution of C-7 CBZ baccatin III.

B. Production of the 3-Phenylisoserine Side Chain

The production of the C3' N-CBZ C-2' benzyl-type protected (2R,3S)-3-phenylisoserine side chain has been previously disclosed in the co-pending patent application Ser. No. 08/609,083 entitled "Intermediate for Docetaxel Synthesis and Production Method Therefor". This compound has the general formula:

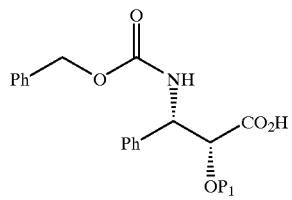

Here, the protecting group on the C-2' hydroxyl is a hydrogenable protecting group such as benzyloxymethyl (BOM) or benzyl.

C. Esterification of C-7 CBZ Baccatin III and the Side Chain

Esterification of C-7 CBZ baccatin III with the C-3' N-CBZ C-2'-protected (2R,3S)-3-phenylisoserine side chain (where the C-2' hydroxyl is protected by any hydrogenable protecting group) may be accomplished as follows. The preferred hydrogenable benzyl group shown below is BOM (benzyloxymethyl). The useful reaction is diagrammed:

Reaction III

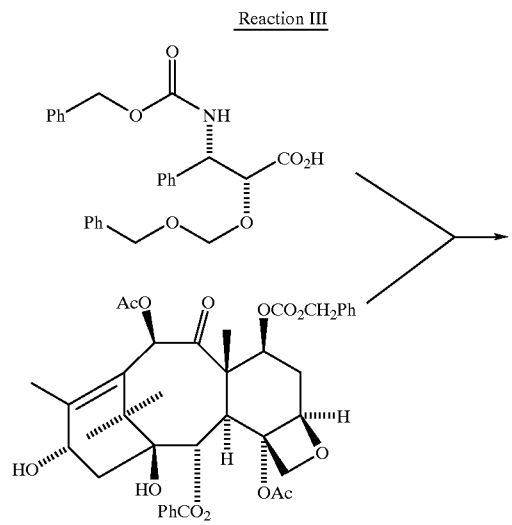

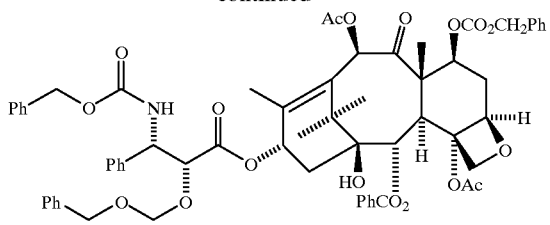
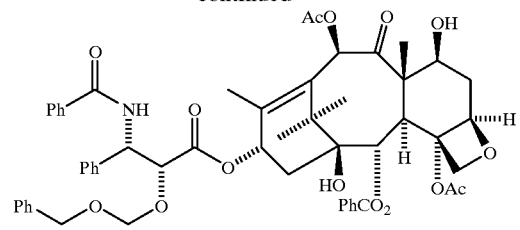

Here the C-7 CBZ baccatin III (1 equivalent) and the acid side chain (6 equivalents) are dissolved in toluene. To this mixture, 0.5 equivalents of DMAP (dimethylamino pyridine) and preferably 6 equivalents of dicyclohexylcarbodiimide (DCC) are added, and the resulting mixture heated at 70° C. for thirty (30) minutes to one (1) hour although the range of temperature could be 60° C. to 80° C. It should also be noted however that other dialkyl carbodiimides may be substituted for the DCC, with one example being diisopropylcarbodiimide.

Next, the solution is cooled to room temperature and an equal volume of ethyl acetate or diethyl ether is added to the solution. The resulting mixture is then cooled to 0° C. and held at this temperature for twenty-four (24) hours. After this time it is filtered, and the residue is rinsed with either diethyl ether or ethyl acetate. The combined organics are then washed with hydrochloric acid (5%), water, and finally brine. The organic phase is separated, dried and concentrated under vacuum. The resulting residue is then dissolved in ethyl acetate:hexane and eluted over a silica gel plug. The eluent is then concentrated under vacuum to result in the esterified compound:

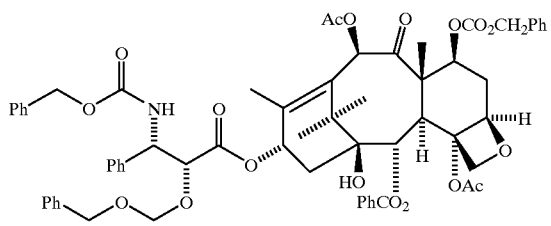

D. Deprotection to Paclitaxel

The esterified compound, above, may now be converted into paclitaxel by removing the nitrogen and C-7 CBZ groups, putting the benzoyl group onto the nitrogen, and finally removing the C-2' benzyl-type protecting group. Removal of the CBZ groups, and subsequent addition of the benzoyl group to the nitrogen are accomplished as follows (BOM is shown as the protecting group at the C-2' hydroxyl site, although benzyl could also be used):

Reaction IV

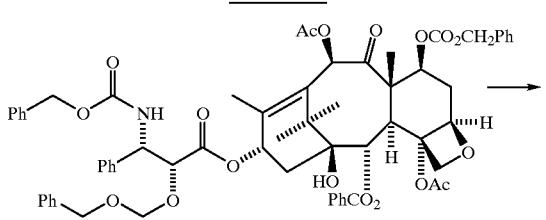

Here, the coupled product of formula 3 is dissolved in isopropanol to which the Pearlman's catalyst is added The resulting mixture is hydrogenated at 40 psi for twenty-four hours, although alternatively, the mixture can be stirred under one atmosphere of hydrogen for 24 hours. Thereafter, the mixture is filtered through diatomaceous earth and reduced under vacuum to residue. Preferably, the residue is taken up in toluene and anhydrous potassium carbonate added. Alternatively, the residue may be taken up in ethyl acetate or toluene and a tertiary amine base, such as triethylamine, is added. In either case, benzoyl chloride is then added dropwise, and the mixture stirred for two hours. The resulting mixture is then washed with water and finally brine. The resulting organic phase is then separated, dried, and concentrated under vacuum to yield C-2' BOM paclitaxel.

Finally, the C-2' BOM is removed according to the following reaction:

Reaction V

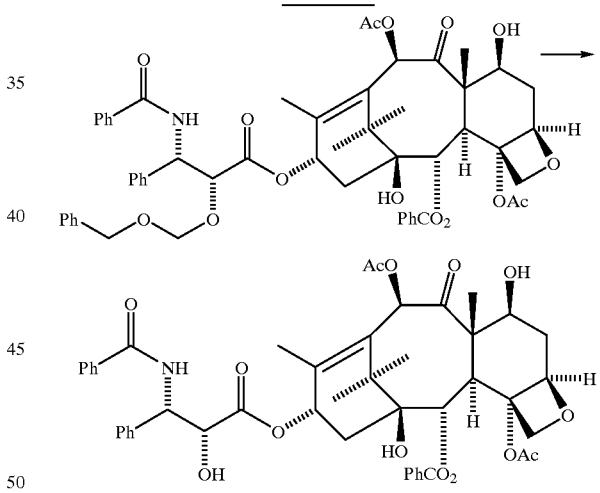

The BOM protected paclitaxel is dissolved in isopropanol to which Pearlman's catalyst is added. This mixture is hydrogenated for 24 hours under 40 psi hydrogen to yield paclitaxel.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A chemical compound for use in the production of taxanes and intermediates therefor having the formula:

wherein R is an alkyl group.

2. A chemical compound according to claim 1 wherein R is a methyl group.

3. A method of producing a compound having a formula:

wherein R is an alkyl group, from a starting compound selected from a group consisting of baccatin III and 10-deacetylbaccatin III comprising the steps of:
- (a) dissolving said starting compound in a first solvent to form a first solution;
- (b) cooling the first solution to a temperature of −20° C. or less;
- (c) thereafter adding to the first solution an alkyl lithium base thereby to form an intermediate compound having a lithium alkoxide at the C-7 position thereof;
- (d) selectively acylating at the C-10 position any of said first intermediate compound present in the first solution where the intermediate compound does not already have an acetyl group at the C-10 position thereby to produce a second solution of C-7 lithium alkoxide of baccatin III; and
- (e) thereafter adding CBZ-Cl to the second solution to form a third solution of C-7 CBZ baccatin III.

4. A method of producing a compound according to claim 3 wherein the first solvent is tetrahydrofuran.

5. A method of producing a compound according to claim 3 wherein the first solution is cooled to at least −40° C.

6. A method of producing a compound according to claim 3 including the step of warning the third solution to 0° C. over a selected interval of time.

7. A method of producing a compound according to claim 6 wherein the selected interval of time is one hour.

8. A method of producing a compound according to claim 3 wherein the alkyl lithium base is n-butyl lithium.

9. A method of producing a compound according to claim 3 wherein the starting compound is 10-deacetylbaccatin III and at least two equivalents of the alkyl lithium base is added to the first solution.

10. A method of producing a compound according to claim 3 including the step of quenching the third solution with an agent effective to eliminate excess of the alkyl lithium base and excess of the CBZ-Cl thereby to form a fourth solution.

11. A method of producing a compound according to claim 10 including the step of concentrating the C-7 CBZ baccatin III from the fourth solution to a first residue.

12. A method of producing a compound according to claim 11 including the step of purifying the C-7 CBZ baccatin III from said first residue.

13. A method of producing a compound according to claim 12 wherein the step of purifying the C-7 CBZ baccatin III is accomplished by a purification step selected from a group consisting of column chromatography and recrystallization.

14. A method of producing a compound according to claim 3 wherein R is a methyl group.

* * * * *

UNITED STATES PATENT AND TRADEMARK OFFICE
CERTIFICATE OF CORRECTION

PATENT NO.     : 6,133,462
DATED          : October 17, 2000
INVENTOR(S)    : Nicholas J. Sisti et al.

Page 1 of 1

It is certified that error appears in the above-identified patent and that said Letters Patent is hereby corrected as shown below:

<u>Title page,</u>
Item [75], the correct listing of Inventors, should be as follows:

-- Nicholas J. Sisti, Boulder, Colo;
  Charles S. Swindell, Merion, Pa.;
  Madhavi C. Chander, Boulder, Colo. --

Signed and Sealed this

Eleventh Day of May, 2004

JON W. DUDAS
*Acting Director of the United States Patent and Trademark Office*